United States Patent
Reime

(10) Patent No.: US 9,002,589 B2
(45) Date of Patent: Apr. 7, 2015

(54) OPTICAL MEASURING DEVICE FOR A VEHICLE AND CORRESPONDING VEHICLE

(76) Inventor: Gerd Reime, Bühl (DE)

(*) Notice: Subject to any disclaimer, the term of this patent is extended or adjusted under 35 U.S.C. 154(b) by 0 days.

(21) Appl. No.: 14/344,604

(22) PCT Filed: Sep. 7, 2012

(86) PCT No.: PCT/EP2012/003750
§ 371 (c)(1),
(2), (4) Date: Mar. 12, 2014

(87) PCT Pub. No.: WO2013/037465
PCT Pub. Date: Mar. 21, 2013

(65) Prior Publication Data
US 2014/0324298 A1    Oct. 30, 2014

(30) Foreign Application Priority Data

Sep. 12, 2011   (DE) .................. 10 2011 112 907

(51) Int. Cl.
| | | |
|---|---|---|
| B60R 22/00 | (2006.01) | |
| E05F 15/20 | (2006.01) | |
| G01V 8/20 | (2006.01) | |
| B60R 16/00 | (2006.01) | |
| G01N 21/55 | (2014.01) | |

(52) U.S. Cl.
CPC ............ *E05F 15/203* (2013.01); *G01V 8/20* (2013.01); *B60R 16/00* (2013.01); *E05F 2015/2061* (2013.01); *E05Y 2900/546* (2013.01); *E05Y 2400/82* (2013.01); *E05Y 2400/852* (2013.01); *E05Y 2400/858* (2013.01); *E05Y 2800/21* (2013.01); *E05F 15/2023* (2013.01); *G01N 21/55* (2013.01)

(58) Field of Classification Search
CPC ..................... B60J 5/00; E05F 15/00

USPC ................... 701/49, 36; 296/146.4
See application file for complete search history.

(56) References Cited

U.S. PATENT DOCUMENTS 8,788,152 B2 *   7/2014   Reimann et al. ............ 701/49
2008/0296926 A1 * 12/2008   Hanzel et al. ............ 296/146.1

FOREIGN PATENT DOCUMENTS

| DE | 10 2004 041 709 C5 | 10/2005 |
|---|---|---|
| EP | 1 902 912 A1 | 3/2008 |
| EP | 2 159 362 A1 | 3/2010 |
| JP | H10 219770 A | 8/1998 |
| JP | 2008-241428 | 10/2008 |
| JP | 2009-14497 | 1/2009 |

* cited by examiner

*Primary Examiner* — Thomas G Black
*Assistant Examiner* — Luke Huynh
(74) *Attorney, Agent, or Firm* — Rabin & Berdo, P.C.

(57) ABSTRACT

An optical measuring device for a vehicle includes an optical transmitter that generates transmitter radiation and radiates it into a monitoring region, and a receiver that receives resulting receiver radiation from the region. An evaluation and control unit evaluates the receiver radiation for object recognition. A first transmitter generates a first light field on a surface in the region by emitting directed first transmitter radiation and a second transmitter generates a second light field in the adjacent surroundings of the first field by emitting directed second transmitter radiation. The unit receives and evaluates first receiver radiation reflected by the first field and second receiver radiation reflected by the second field via the receiver, wherein the unit generates an output signal when it detects change in the reflected second receiver radiation caused by a trigger object detected in the region and reflected first receiver radiation unchanged by the object.

20 Claims, 3 Drawing Sheets

OPTICAL MEASURING DEVICE FOR A VEHICLE AND CORRESPONDING VEHICLE

BACKGROUND OF THE INVENTION

1. Field of the Invention

The invention relates to an optical measuring device for a vehicle of the type mentioned in the first part of claim 1 and also to an appertaining vehicle comprising such an optical measuring device.

2. Description of the Related Art

From patent application EP 1 902 912 A1 for example, there is known a motor vehicle comprising a sensor device which monitors parts of an external area of the motor vehicle for the presence of a body-part of a person or of an object. For this purpose, the sensor device is attached and oriented in such a way that a part of a leg or a foot of a person standing beside the motor vehicle is moveable by means of a simple body movement such as raising and/or swinging the leg or foot for example into the part of the triggering region of the motor vehicle that is being monitored by the sensor arrangement. Then, after successful authentication of the person, a corresponding process opens a door, a bonnet and/or a boot if the body movement in the monitored area is recognized.

In patent specification DE 10 2004 041 709 C5 for example, there is known a vehicle having an automatically opening flap. The vehicle described comprises a flap that opens automatically in response to an opening command wherein the opening command is produced without manual actuation of an unlocking and/or locking mechanism, and also comprises a proximity sensor and a control device that is actively connected to an unlocking and/or locking mechanism for the automatically opening flap on the one hand and to the proximity sensor on the other. The control device is constructed in such a manner that it recognizes the presence of a valid access authorization means within a surrounding region and, upon recognizing a valid access authorization means, activates the unlocking and/or locking mechanism for enabling the automatically opening flap in dependence on the presence of an unlocking signal from the proximity sensor. The proximity sensor is arranged on the vehicle in such a manner that its direction of sensitivity for the detection of objects is directed downwardly towards the surface of the road so that a person can switch on the proximity sensor by swinging his foot in the area between the vehicle bodywork and the road surface.

The solutions described presuppose that the person knows the exact position of the sensor arrangement or the proximity sensor and the appertaining detection region in order to enable the requisite switching signal to be produced by the movement described.

SUMMARY OF THE INVENTION

The object of the invention is to provide an optical measuring device for a vehicle which enables simplified triggering of a switching process without manual actuation and without the need for a predetermined gesture as well as to provide a corresponding vehicle comprising such an optical measuring device.

In accordance with the invention, this object is achieved by an optical measuring device for a vehicle incorporating the features of Claim 1 and by a vehicle incorporating the features of Claim 13. Further features presenting the embodiments of the invention in advantageous manner are contained in the appendant Claims.

The basic concept of the invention is based on the principle that two light fields are projected onto a surface in a monitored area and the reflections from the surface are detected and evaluated. The change of reflection of just one particular light field then triggers a switching process if the reflections of a further light field are not affected.

The advantage obtained by means of the invention is that, without gesturing, a process such as opening a flap, an entry door and/or a cover for example can be triggered merely by a change of reflection in a monitored area, whereby the monitored area can be protected from unwanted false triggering actions due to animals and/or objects entering the monitored area inadvertently for example by the shape of the predetermined visible light field.

Embodiments of the present invention provide an optical measuring device for a vehicle which comprises at least one optical transmitter that produces a transmitter radiation and radiates it into a monitored area, and at least one optical receiver which receives a resultant receiver radiation from the monitored area, wherein an evaluating and control unit evaluates the receiver radiation for the purposes of identifying an object. In accordance with the invention, at least one first optical transmitter produces a first light field having a predetermined shape on a surface in the monitored area by emitting a first directional transmitter radiation and at least one second optical transmitter produces a second light field having a predetermined shape in the neighbouring surroundings of the first light field by emitting a second directional transmitter radiation, wherein, via the at least one optical receiver, the evaluating and control unit receives and evaluates a first receiver radiation reflected by the surface of the first light field and a second receiver radiation reflected by the surface of the second light field, and wherein the evaluating and control unit produces an output signal if the evaluating and control unit recognizes a change of the reflected second receiver radiation which is caused by a triggering object being detected in the monitored area and a first receiver radiation which is being reflected unchanged by the triggering object.

Embodiments of the optical measuring device in accordance with the invention are employed as surroundings monitoring devices in a vehicle, in particular a motor vehicle, in order to open a flap automatically without manual actuation. In addition to the surroundings monitoring device, a vehicle in accordance with the invention comprises an access authorization system, at least one flap comprising an opening mechanism, and a control device which produces an opening command in dependence on an access authorization recognized by the access authorization system and an output signal produced by the surroundings monitoring device and sends said opening command to the opening mechanism of the at least one flap which automatically opens the flap without manual actuation.

An object introduced into one of the two light fields functioning as detection fields alters the reflection of the corresponding light field and can thus be detected. The detection fields are oriented in one direction so that a person can, for example, deliberately insert his foot into the detection region of the optical measuring device in such a way that the second light field is at least partially covered and the first light field is not touched. The second receiver radiation reflected by the second light field or detection field is thereby altered and the evaluating and control unit recognizes the resulting intensity difference during the evaluation process. The first receiver radiation reflected by the first light field or detection field remains uninfluenced so that the evaluating and control unit recognizes the constant intensity of the first receiver radiation during the evaluation process.

If an unauthorized object such as e.g. an animal, a ball etc. traverses the detection region of the optical measuring device, then this leads to changes of reflection in the first light field or detection field and in the second light field or detection field. This means that both the intensity of the first receiver radiation as well as that of the second receiver radiation will change. The evaluating and control unit recognizes these intensity differences during the evaluation process and concludes that an inadvertent or unauthorized effect on the light fields has occurred so that no output signal is produced.

Embodiments of the present invention thus make it possible in an advantageous manner for a vehicle user who is approaching his vehicle but does not have a hand free for manually triggering an opening process for the vehicle flap due to the fact that he is carrying something to automatically open the corresponding flap without an additional manual actuation by deliberately moving an object, preferably his foot, into the detection region of the optical measuring device. The authorization for the triggering of the opening process is thereby determined by the access authorization system which checks as to whether a portable authenticating element assigned to the vehicle such as an electronic ignition key for example, is located in the detection region of the access authorization system. The access authorization system carries on a corresponding encoded data communication process with the authenticating element over a communication connection and sends the access authorization signal to the control device after a positive authenticating process.

In a preferred embodiment of the present invention, at least one of the two light fields is visibly marked on the surface. For this purpose, at least one of the two optical transmitters can radiate a transmitter radiation in the visible light spectrum. Alternatively, the first and second optical transmitter can each radiate a transmitter radiation in the non-visible light spectrum and a third transmitter can be provided for radiating a transmitter radiation in the visible light spectrum and marking the corresponding light field on the surface. Preferably, the second light field is visibly marked on the surface either by the second optical transmitter or by the third optical transmitter. The visible appearance of at least one of the two light fields facilitates the process of finding the detection region and thus of producing the output signal and triggering an opening process.

In one advantageous embodiment of the measuring device in accordance with the invention, the shape of the first light field is such that it is open on one side, it preferably having a U-shape or a horseshoe shape which can be composed of a plurality of light spots. In advantageous manner, the open U-shape or horseshoe shape bears a great resemblance to a shod human foot which can preferably be moved into the first light field from the open end for the purposes of producing the output signal without touching the first light field so that the first light field frames the shod foot. The at least one first optical transmitter may comprise a respective emitter diode for producing each of the individual light spots. For the purposes of depicting the open shape on the surface in the monitored area, the emitter diodes may be provided with differing predetermined radiant angles. Alternatively, for the purposes of producing the individual light spots, the at least one first optical transmitter may comprise just one emitter diode and an optical system which distributes the light from the emitter diode over different predetermined radiant angles and so produces the individual light spots on the surface in the monitored area.

In a further advantageous embodiment of the measuring device in accordance with the invention, the second light field can be produced in the form of a single light spot of a predetermined diameter. The second light field is preferably arranged at the open end of the first light field and is at least partially surrounded by the first light field. The arrangement of the two light fields on the surface in the monitored area occurs in advantageous manner in such a way that the second light field implemented in the form of a single light spot has predetermined spacings from the individual light spots of the first light field. This enables the output signal to be produced in a particularly simple manner when the shod foot is introduced from the rear into the open region of the first light field and thereby simultaneously covers the second light field so that the first receiver radiation reflected from the first light field remains uninfluenced by the triggering object such as the shod foot for example, whereas the second light field is at least partly covered by the triggering object and the second receiver radiation reflected from the second light field is affected. In order to produce the single light spot of the second light field at a desired point on the surface in the monitored area, the at least one second optical transmitter may comprise at least one emitter diode which is arranged at a predetermined radiant angle for the purposes of producing the single light spot.

In a further advantageous embodiment of the measuring device in accordance with the invention, the at least one first optical transmitter produces the first transmitter radiation and the at least one second optical transmitter produces the second transmitter radiation in the same frequency range, wherein the first transmitter radiation and the second transmitter radiation are radiated in mutually time displaced manner using a time-division multiplexing process, and wherein the frequency range used comprises frequencies in the visible or the non-visible light spectrum. The use of a time-division multiplexing process enables the reflected first or second receiver radiation to be readily associated with the first or second light field in advantageous manner since the resulting receiver radiations are likewise received in mutually time displaced manner.

In a further advantageous embodiment of the measuring device in accordance with the invention, the at least one first optical transmitter produces the first transmitter radiation in a first frequency range, and the at least one second optical transmitter produces the second transmitter radiation in a second frequency range differing from the first frequency range. This likewise enables the reflected first or second receiver radiation to be readily associated with the first or second light field in advantageous manner. Thus, the at least one first optical transmitter may have a first frequency range which includes frequencies in the non-visible light spectrum. A second optical transmitter may have a second frequency range which includes frequencies in the non-visible or the visible light spectrum. This means that the second optical transmitter produces a non-visible second light field or detection field, or a visible second light field or detection field on the surface in the monitored area. Consequently, a third optical transmitter which has a frequency range comprising frequencies in the visible light spectrum can be used for the purposes of marking or rendering visible the second light field or detection field. Thus together, the second and the third optical transmitter produce the visible second light field.

In a further advantageous embodiment of the measuring device in accordance with the invention, the evaluating and control unit controls the at least one first optical transmitter and the at least one second optical transmitter based on the Halios measurement principle and evaluates the first and second receiver radiations received from the at least one optical receiver for the purposes of identifying an object in accordance with the Halios measurement principle. The Halios measurement principle comprises an optical transmitter for the production of a detection field, an optical compensation transmitter, an optical receiver, a synchronous demodulator and at least one regulator. In this connection, the optical transmitter sends out rectangular amplitude-modulated transmitted luminous radiation. By virtue of a reflection process in the detection field, a portion of this light reaches the optical receiver in the form of received luminous radiation. In like manner, the optical compensation transmitter sends out rectangular amplitude-modulated compensation luminous radiation directly to the optical receiver which however is phase-shifted by exactly 180° with respect to the transmitted luminous radiation. At the optical receiver, the received luminous radiation is superimposed on the compensation luminous radiation and the two luminous radiations cancel each other out as an equal signal if they have exactly the same amplitude. Consequently, the synchronous demodulator can easily detect which of the optical transmitters is transmitting stronger signals. The synchronous demodulator supplies this information to the at least one regulator which adjusts the transmission amplitude of the compensation transmitter in such a way as to complement the received luminous radiation and thereby re-establish an amplitude difference of zero. Now if the reflection behaviour of the detection field changes, then this leads to a corresponding change in the reflected received luminous radiation which reaches the optical receiver from the optical transmitter via the detection field. This immediately causes the intensity of the optical compensation transmitter to be adjusted by the at least one regulator in order to continue to fulfil the regulating conditions. This adjustment causes a change in the regulating signal which is functioning as an output signal. Thus, the regulating signal represents a measure for the reflection of the detection field. Since embodiments of the present invention comprise at least two optical transmitters, a regulator is provided for each optical transmitter.

In one advantageous embodiment of the vehicle in accordance with the invention, the first light field can be produced on the surface in the monitored area in such a way that the open-side of the shaped first light field being produced faces away from the vehicle.

In a further advantageous embodiment of the vehicle in accordance with the invention, the automatically opening flap is an entry door and/or a tail gate and/or a boot lid of the vehicle for example.

In a further advantageous embodiment of the vehicle in accordance with the invention, the predetermined radiant angles of the emitter diodes of the at least one first optical transmitter and of the at least one second optical transmitter that are used for the production of the individual light spots can be predetermined in advantageous manner in such a way that the second light field is arranged on the road surface at the open end of the first light field in the surroundings of the corresponding automatically-opening flap, and is at least partly surrounded by the first light field, wherein the individual light spots of the first light field have predetermined spacings from the single light spot of the second light field.

In a further advantageous embodiment of the vehicle in accordance with the invention, the evaluation and control unit produces the output signal if a triggering object, preferably a foot, at least partly covers the second light field without touching the first light field.

Exemplary embodiments of the invention are described in more detail hereinafter with the aid of a graphical illustration. In the drawings, the same reference symbols apply to components or elements which implement the same or analogous functions.

DETAILED DESCRIPTION OF PREFERRED EXEMPLARY EMBODIMENTS

The invention is now exemplarily described in more detail with reference to the accompanying drawings. Nevertheless, the exemplary embodiments are merely examples which are not intended to limit the inventive concept to a certain arrangement. Before the invention is described in detail, it should be pointed out that it is not limited to the particular components of the device or the particular processing steps since these components and processes can vary. The terms used here are only intended to describe particular embodiments and are not used in a restrictive manner. Moreover, where the singular or indefinite articles are used in the description or in the Claims, this also refers to the plural form of these elements insofar as the general context does not unambiguously signify something to the contrary.

Figure 1:
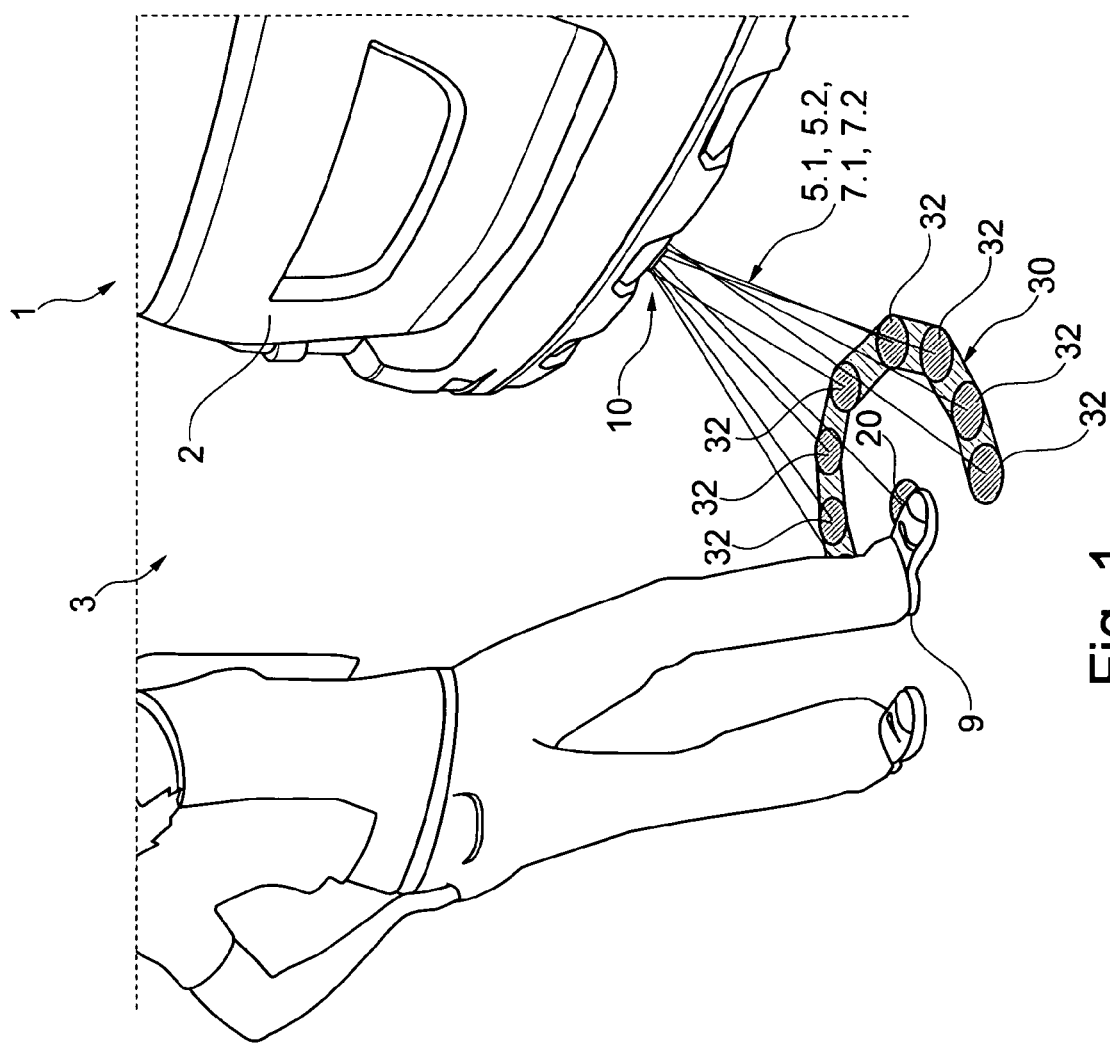
FIG. 1 shows a schematic perspective illustration of a rear part of a vehicle which comprises an exemplary embodiment of an optical measuring device in accordance with the invention.
Figure 2:
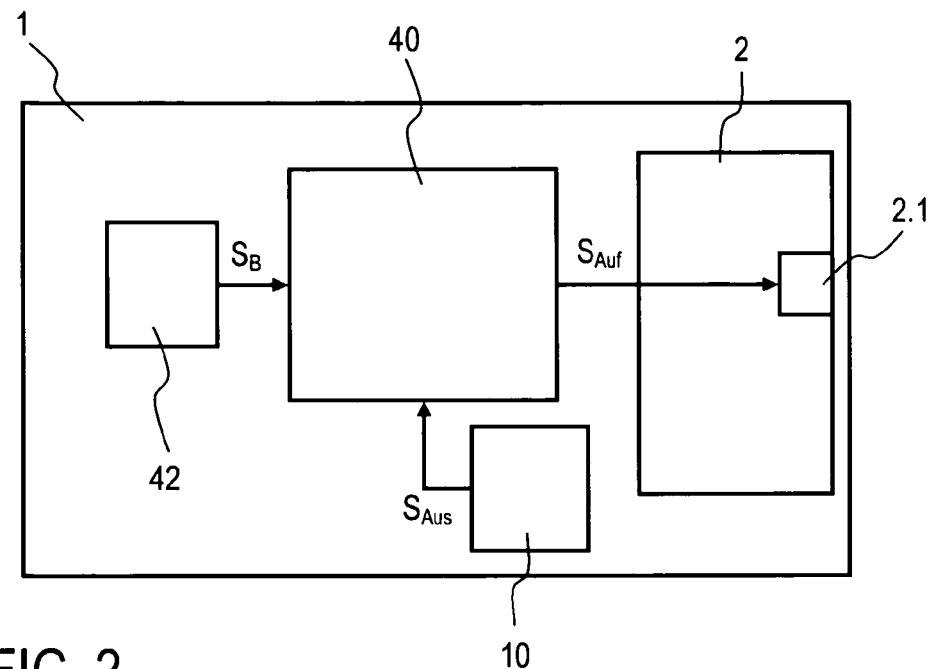
FIG. 2 a schematic block diagram of the vehicle depicted in FIG. 1.
Figure 3:
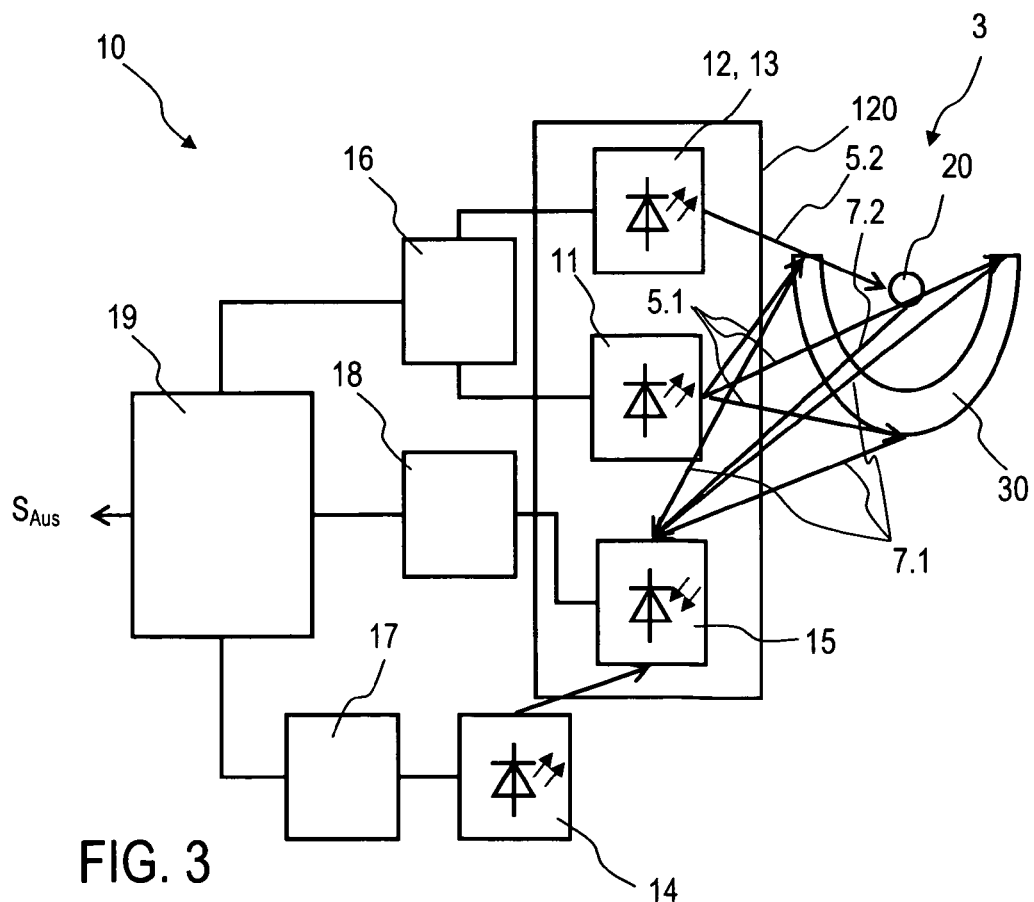
FIG. 3 A schematic block diagram of the exemplary embodiment of the optical measuring device for a vehicle in accordance with the invention depicted in FIG. 1.

As is evident from FIGS. 1 to 3, the vehicle 1 in the illustrated exemplary embodiment is a motor vehicle and comprises an access authorization system 42, at least one flap 2 comprising an opening mechanism 2.1, a surroundings monitoring device 10 and a control device 40. The control device 40 produces an opening command $S_{Auf}$ in dependence on an access authorization signal $S_B$ produced by the access authorization system 42 and an output signal $S_{Aus}$ produced by the surroundings monitoring device 10, and it sends this signal to the opening mechanism 2.1 of the at least one flap 2 which automatically opens the flap 2 without manual actuation.

From the state of the art, there are known various embodiments of access authorization systems 42 which check the authorization for the triggering of an opening process for at least one flap 2 by means of an appropriate encoded data communication with a portable authenticating element which is assigned to the vehicle 1 and is located in the detection region of the access authorization system 42. Consequently, one can dispense here with a detailed description of the access authorization system 42. For the present invention, use is merely made of the access authorization signal $S_B$ which represents the result of a positive authentication of the person involved. If a justified authenticating element such as an electronic vehicle key for example is located in the detection region of the access authorization system 2, then the access authorization system 42 sends the access authorization signal $S_B$ to the control device 40. An automatic opening process for the at least one flap 2 can then be initiated if the surroundings monitoring device 10 is producing the output signal $S_{Aus}$ and sending it to the control device 40.

The surroundings monitoring device 10 is implemented as an optical measuring device which comprises at least one optical transmitter 11, 12, 13, 14 that produces a transmitter radiation 5.1, 5.2 and radiates it into a monitored area 3, and at least one optical receiver 15 which receives a resulting receiver radiation 7.1, 7.2 from the monitored area. An evaluating and control unit 19 evaluates the receiver radiation 7.1, 7.2 for the purposes of identifying an object.

In accordance with the invention, at least one first optical transmitter 11 produces a first light field 30 of a predetermined shape on a surface in the monitored area 3 by emitting a first directional transmitter radiation 5.1 and at least one second optical transmitter 12, 13 produces a second light field 20 of a predetermined shape in the neighbouring surroundings of the first light field 30 by emitting a second directional transmitter radiation 5.2. Via the at least one optical receiver 15, the evaluating and control unit 19 receives a first receiver radiation 7.1 reflected by the surface of the first light field 30 and a second receiver radiation 7.2 reflected by the surface of the second light field 20. During the evaluation process, the evaluating and control unit 19 produces the output signal $S_{Aus}$ if it recognizes that there is a change of the reflected second receiver radiation 7.2 caused by a triggering object 9 being detected in the monitored area 3 and if there is a reflected first receiver radiation 7.1 that is unchanged by the triggering object 9.

As is further evident from FIG. 1, the non-visible first light field 30 or detection field in the exemplary embodiment illustrated here has a shape that is open on one side, preferably a U-shape and/or a horseshoe shape, which is composed of a plurality of non-visible light spots 32. The visible second light field 20 or detection field is a single visible light spot of a predetermined diameter which is arranged at the open end of the first light field 30 or detection field and is at least partly surrounded by the first light field 30 or detection field. The single light spot of the second light field 20 i.e. a detection field is located at predetermined spacings from the individual light spots 32 of the first light field 30 i.e. a detection field. As is further evident from FIG. 1, the first light field 30 is produced on the road surface in such a way that the open side of the shaped first light field 30 or detection field faces away from the vehicle 1. In the illustrated exemplary embodiment, the two light fields 20, 30 are produced on the road surface in the rear region of the vehicle 1 in order to automatically open the automatically opening flap 2 that is implemented as a tail gate. In not illustrated embodiments of the present invention, the two light fields 20, 30 could also be produced on the road surface in the region of an entry door and/or a boot lid in order to trigger an automatic process for opening the corresponding flap 2.

A triggering object 9 moved into one of the two light fields 20, 30 i.e. the detection fields alters the reflection of the corresponding light field 20, 30 and can thus be detected. The two light fields 20, 30 i.e. the detection fields are oriented in one direction so that a person can place an e.g. shod foot 9 on the second light field 20 i.e. a detection field which is implemented as a light spot in such a way that the triggering object 9 i.e. the foot does not affect the second light field 30 i.e. the detection field. If an object such as an animal or a ball for example traverses the monitored area 3, this leads to changes of reflection in both of the light or detection fields 20, 30, i.e. both within the region of the first U-shaped light or detection field 30 as well as within the region of the second light field 20 i.e. the detection field implemented in the form of a light spot. However, if the triggering object 9, here the foot, is introduced from the rear into the open region of the first U-shaped light or detection field 30, then a distinguishable action only takes place in the second light field 20 i.e. the detection field implemented in the form of a light spot.

Figure 4:
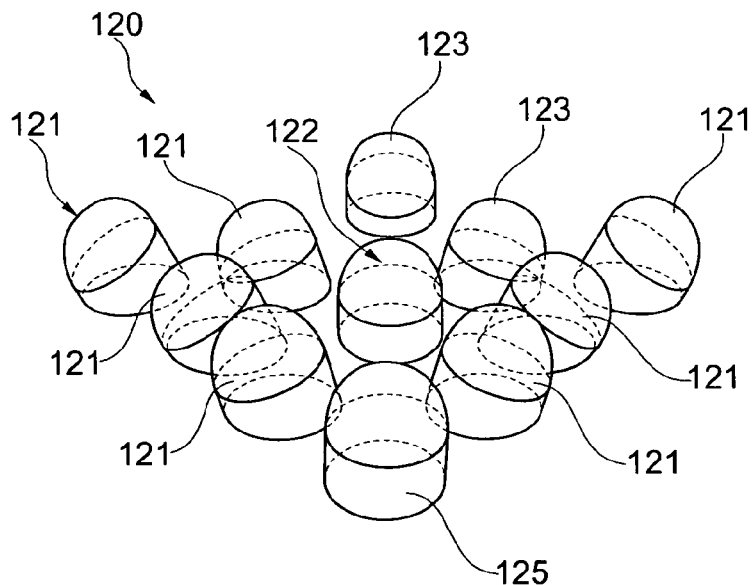
FIG. 4 a schematic perspective illustration of a sensor arrangement for the exemplary embodiment of the optical measuring device for a vehicle in accordance with the invention that is illustrated in FIGS. 1 and 2, FIG. 5 a block diagram alternative to that of FIG. 3 when using a camera and a pixel evaluation process.

As is further evident from FIGS. 3 and 4, the optical measuring device 10 for a vehicle 1 measures reflections of the two light fields 20, 30 i.e. the detection fields with the optical receiver 15 that is arranged in a sensor arrangement 120 and is implemented as a photodiode 125 or a correspondingly connected LED or as a camera 15' for example. The sensor arrangement 120 comprises the first optical sensor 11 which incorporates a plurality of light emitting diodes 121 that are arranged at particular angles relative to each other and are each at a predetermined radiant angle in order to project the desired shape of the first light field 30 such as a U-shape or a horseshoe shape for example onto the road surface in the monitored area 3. In a not illustrated alternative embodiment, the at least one first optical transmitter 11 used for the production of the individual light spots 32 comprises just one emitter diode and an optical system which distributes the light from the emitter diode over different predetermined radiant angles in order to project the individual light spots of the first light field 30 onto the road surface in the desired shape.

In the illustrated exemplary embodiment, the light emitting diodes 121 of the first optical transmitter 11 produce the first transmitter radiation 5.1 in a first frequency range which comprises frequencies in the non-visible light spectrum such as the infrared frequency range for example. Moreover, the transmitter arrangement 120 comprises the second optical transmitter 12 which comprises an infrared diode 122 that has a predetermined radiant angle in order to project the desired shape of the second light field 20 such as a spot of a predetermined diameter for example onto the road surface within the surroundings of the first light field 30. In the illustrated exemplary embodiment, the projection process takes place in the infrared frequency range i.e. in a range that is not visible to the human eye. For the purposes of distinguishing the resulting receiver radiations 7.1, 7.2, the first transmitter radiation 5.1 and the second transmitter radiation 5.2 are radiated in mutually time displaced manner by using a time-division multiplexing process. This enables the reflected receiver radiations 7.1, 7.2 to be more easily associated with the first or second light field 30, 20. For the purposes of making the second light field 20 more visible, the sensor arrangement 120 comprises a third optical transmitter 13 which incorporates an e.g. laser diode 123 that has a predetermined radiant angle in order to mark the desired shape of the second light field 20 such as a spot of a predetermined diameter for example on the road surface within the surroundings of the first light field 30 and thus make it visible to the user. Consequently, the laser diode 123 of the third optical transmitter 13 produces luminous radiation in the frequency range of the visible light spectrum.

In a not illustrated alternative embodiment of the measuring device 10 in accordance with the invention, the at least one first optical transmitter 11 produces the first transmitter radiation 5.1 in a first frequency range, and the at least one second optical transmitter 12 produces the second transmitter radiation 5.2 in a second frequency range differing from the first frequency range. In advantageous manner, this likewise makes it possible to easily associate the reflected first and second receiver radiation 7.1, 7.2 with the first and second light field 30, 20 respectively. The at least one first optical transmitter 11 may therefore use a first frequency range comprising frequencies in the non-visible light spectrum. A second optical transmitter 12 can have a second frequency range comprising frequencies in the non-visible or the visible light spectrum. This means that the second optical transmitter 12 can produce a non-visible second light field 20 i.e. a detection field or a visible second light field 20 i.e. a detection field on the surface in the monitored area 3. Here too, the third optical transmitter 13 can be used for marking or rendering visible the second light field 20 i.e. the detection field, if the second optical transmitter 12 is radiating the second transmitter frequency 5.2 in the non-visible light spectrum.

Due to the predetermined radiant angles of the emitter diodes 121, 122, 123 of the first optical transmitter 11 as well as the second and third optical transmitters 12, 13, the individual light spots 20, 32 of the two light fields 20, 30 i.e. the detection fields can be predetermined in such a way that the second light field 20 is arranged on the road surface in the surroundings of the corresponding automatically-opening flap 2 at the open end of the first light field 30 and is at least partially surrounded by the first light field 30, wherein the individual light spots 32 of the first light field 30 are located at predetermined spacings from the single light spot of the second light field 20.

As is further evident from FIG. 3, the evaluating and control unit 19 controls the at least one first optical transmitter 11 and the at least one second optical transmitter 12 on the basis of the Halios measurement principle and evaluates the receiver radiation 7.1, 7.2 received by the at least one optical receiver 15 for the purposes of identifying an object in accord with the Halios measurement principle.

For this purpose, the optical measuring device 10 comprises a fourth optical transmitter 14 which incorporates at least one compensation light emitting diode, a first modulator 16 for modulating the first optical transmitter 11 and the second optical transmitter 12, a second modulator 17 for modulating the fourth optical transmitter 14 and a synchronous demodulator 18. In order to utilise the Halios measurement principle, the fourth optical transmitter 14 includes a not illustrated compensation light emitting diode for the first optical transmitter 11 and for the second optical transmitter 12 which are likewise operated in a time division multiplex process in analogous manner to the first optical transmitter 11 and the second optical transmitter 12. This means that the compensation light emitting diode is used during a time slot associated with the first optical transmitter 11 for the purposes of compensating the first optical transmitter 11 and during a time slot associated with the second optical transmitter 11 for the purposes of compensating the second optical transmitter 12. The first and second optical transmitters 11, 12 are respectively modulated by the first modulator 16 and radiate rectangular amplitude-modulated first and second transmitter radiations 5.1, 5.2. By means of a reflection process at the first light field 30, a portion of the first transmitter radiation 5.1 arrives at the optical receiver 15 in the form of a reflected first receiver radiation 7.1, and by means of a reflection at the second light field 20, a portion of the second transmitter radiation 5.2 arrives at the optical receiver 15 in the form of a reflected second receiver radiation 7.2. The compensation light emitting diode likewise sends out rectangular amplitude-modulated luminous radiations to the optical receiver 15, but they however are phase-shifted by exactly 180° relative to the first and second transmitter radiations 5.1, 5.2. At the receiver 15, the first transmitter radiation 5.1 and the second transmitter radiation 5.2 are superimposed in time displaced manner on the luminous radiation produced by the compensation light emitting diode and cancel each other out as equal signals if they have exactly the same amplitude. The synchronous demodulator 18 can thereby easily detect whether the first optical transmitter 11 or the compensation light emitting diode, or the second optical transmitter 12 or the compensation light emitting diode is transmitting a stronger signal. The synchronous demodulator 18 supplies this information to the evaluating and control unit 19 which adjusts the transmission amplitude of the compensation light emitting diode by means of a first regulator in such a way that the first receiver radiation 7.1 and the luminous radiation produced by the compensation light emitting diode are refreshed so as to re-establish an amplitude difference of zero and, by means of a second regulator, adjusts the transmission amplitude of the compensation light emitting diode in such a way that the second receiver radiation 7.2 and the luminous radiation produced by the compensation light emitting diode are refreshed so as to re-establish an amplitude difference of zero.

Now if the reflection behaviour of the first light or detection field 30 or that of the second light or detection field 20 alters due to the introduction of the triggering object 9 for example, then the evaluating and control unit 19 can recognize these changes in the reflection behaviour in a simple manner by evaluating the regulating signal required for adjusting the amplitude of the compensation light emitting diode since the respective regulating signals represent a measure for the respective reflection at the first and/or second light field 20, 30.

Figure 5:
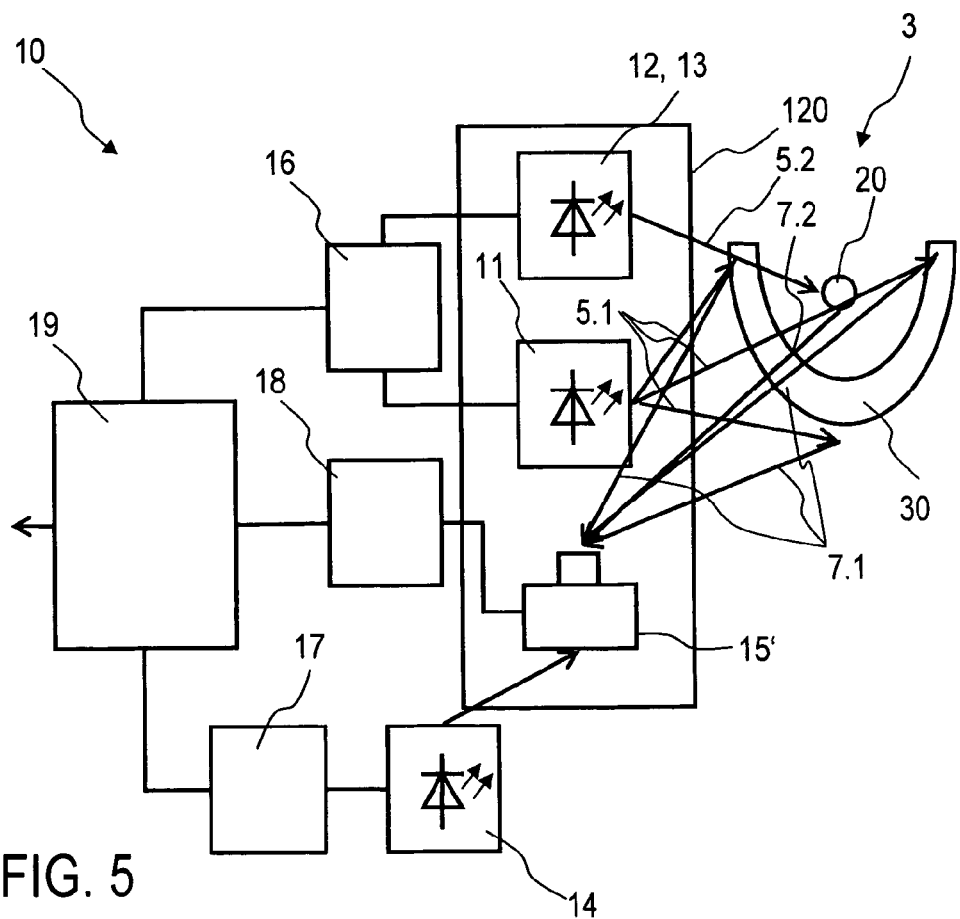

If the optical receiver in accordance with FIG. 5 is formed by at least one camera 15', then the pictures received from the camera are fed to and evaluated by the evaluating and control unit 19 for the purposes of producing the output signal $S_{Aus}$. The evaluation process can be effected by means of a pixel evaluation of the picture pixels for example.

Embodiments of the present invention make it possible in advantageous manner to initiate a process such as the opening of a vehicle flap for example, without the need for a predetermined gesture merely by detecting a change of reflection in a monitored area using two light fields or detection fields, wherein the special shape of the light fields or detection fields protects against false triggering.

It is self-evident that this description can be subjected to the most diverse modifications, changes and adaptations which fall within the range of equivalents to the appended Claims.

The invention claimed is:
1. An optical measuring device for a vehicle, comprising:
at least one optical transmitter which produces a transmitter radiation and radiates it into a monitored area; and
at least one optical receiver which receives a resulting receiver radiation from the monitored area,
wherein an evaluating and control unit evaluates the receiver radiation for the purposes of identifying an object,
wherein at least one first optical transmitter produces a first light field of a predetermined shape on a surface in the monitored area by emitting a first directional transmitter radiation and at least one second optical transmitter produces a second light field of a predetermined shape in the neighbouring surroundings of the first light field by emitting a second directional transmitter radiation,
wherein, via the at least one optical receiver, the evaluating and control unit receives and evaluates a first receiver radiation reflected by the surface of the first light field and a second receiver radiation reflected by the surface of the second light field, wherein the evaluating and control unit produces an output signal if the evaluation and control unit recognizes a change of the reflected second receiver radiation which is caused by a triggering object recognized in the monitored area and a first receiver radiation which is reflected unchanged by the triggering object.

2. A measuring device in accordance with claim 1, wherein the first light field is shaped such as to be open on one side, preferably having a U-shape, and is composed of a plurality of light spots.

3. A measuring device in accordance with claim 2, wherein, for the production of the individual light spots, the at least one first optical transmitter comprises a respective emitter diode each of which is arranged at a different predetermined radiant angle, or at least one emitter diode and an optical system which distributes the light from the emitter diode over differing predetermined radiant angles.

4. A measuring device in accordance with claim 1, wherein the second light field is a single light spot of a predetermined diameter and in that the second light field is preferably arranged at the open end of the first light field and is at least partly surrounded by the first light field.

5. A measuring device in accordance with claim 4, wherein the single light spot of the second light field has predetermined spacings from the individual light spots of the first light field.

6. A measuring device in accordance with 5, wherein, for the purposes of producing the single light spot, the at least one second optical transmitter comprises at least one emitter diode which is arranged at a predetermined radiant angle.

7. A measuring device in accordance with claim 1, wherein the at least one first optical transmitter produces the first directional transmitter radiation and the at least one second optical transmitter produces the second directional transmitter radiation in the same frequency range,
wherein the first transmitter directional radiation and the second transmitter directional radiation are radiated in mutually time displaced manner using a time-division multiplexing process, and
wherein the frequency range used comprises frequencies in the visible or the non-visible light spectrum.

8. A measuring device in accordance with claim 1, wherein the at least one first optical transmitter produces the first directional transmitter radiation in a first frequency range, and the at least one second optical transmitter produces the second directional transmitter radiation in a second frequency range which differs from the first frequency range.

9. A measuring device in accordance with claim 8, wherein the at least one first optical transmitter has a first frequency range comprising frequencies in the non-visible light spectrum, and in that the at least one second optical transmitter has a second frequency range comprising frequencies in the non-visible or the visible light spectrum.

10. A measuring device in accordance with claim 9, wherein, for the purposes of marking the second light field, a third optical transmitter has a frequency range comprising frequencies in the visible light spectrum.

11. A measuring device in accordance with claim 1, wherein the optical receiver is formed by at least one camera, and in that the evaluating and control unit evaluates the pictures received from the camera for the purposes of producing the output signal, in particular, in the form of a pixel evaluation process.

12. A measuring device in accordance with claim 1, wherein the evaluating and control unit controls the at least one first optical transmitter and the at least one second optical transmitter based on the Halios measurement principle and evaluates the receiver radiation received by the at least one optical receiver for the purposes of identifying an object in accordance with the Halios measurement principle.

13. A vehicle, in particular a motor vehicle, comprising an access authorization system, at least one flap which has an opening mechanism, a surroundings monitoring device and a control device which produces an opening command in dependence on an access authorization recognized by the access authorization system and an output signal produced by the surroundings monitoring device and sends it to the opening mechanism of the at least one flap which automatically opens the flap without manual actuation,
wherein the surroundings monitoring device is implemented as an optical measuring device in accordance with claim 1.

14. A vehicle in accordance with claim 13, wherein the open-on-one-side shape of the produced first light field faces away from the vehicle.

15. A vehicle in accordance with claim 13, wherein the automatically opening flap is at least one of an entry door and a tail gate and a boot lid of the vehicle.

16. A vehicle in accordance with claim 13, wherein the predetermined radiant angles of the emitter diodes of the at least one first optical transmitter and of the at least one second optical transmitter that are used for the production of the individual light spots are predetermined in such a way that the second light field is arranged on the road surface at the open end of the first light field in the surroundings of the corresponding automatically-opening flap, and is at least partly surrounded by the first light field, wherein the individual light spots of the first light field have predetermined spacings from the single light spot of the second light field.

17. A vehicle in accordance with claim 13, wherein the evaluating and control unit produces the output signal if a triggering object, preferably a foot, at least partly covers the second light field without touching the first light field.

18. A vehicle in accordance with claim 13, wherein for the production of the individual light spots, the at least one first optical transmitter comprises a respective emitter diode each of which is arranged at a different predetermined radiant angle, or at least one emitter diode and an optical system which distributes the light from the emitter diode over differing predetermined radiant angles.

19. A vehicle in accordance with claim 13, wherein the second light field is a single light spot of a predetermined diameter and in that the second light field is preferably arranged at the open end of the first light field and is at least partly surrounded by the first light field.

20. A vehicle in accordance with claim 13, wherein the at least one first optical transmitter produces the first directional transmitter radiation and the at least one second optical transmitter produces the second directional transmitter radiation in the same frequency range,
wherein the first transmitter directional radiation and the second transmitter directional radiation are radiated in mutually time displaced manner using a time-division multiplexing process, and
wherein the frequency range used comprises frequencies in the visible or the non-visible light spectrum.

* * * * *